(12) United States Patent
Madore (10) Patent No.: US 9,782,290 B2
(45) Date of Patent: Oct. 10, 2017

(54) SIZE-ADJUSTABLE MALE CHASTITY DEVICE

(71) Applicant: Austin Madore, Mulberry, FL (US)

(72) Inventor: Austin Madore, Mulberry, FL (US)

( * ) Notice: Subject to any disclaimer, the term of this patent is extended or adjusted under 35 U.S.C. 154(b) by 324 days.

(21) Appl. No.: 14/428,619

(22) PCT Filed: Oct. 1, 2013

(86) PCT No.: PCT/US2013/062932
§ 371 (c)(1),
(2) Date: Mar. 16, 2015

(87) PCT Pub. No.: WO2014/055567
PCT Pub. Date: Apr. 10, 2014

(65) Prior Publication Data
US 2015/0216717 A1  Aug. 6, 2015

Related U.S. Application Data

(60) Provisional application No. 61/708,801, filed on Oct. 2, 2012.

(51) Int. Cl.
*A61F 6/02* (2006.01)
*A61F 5/00* (2006.01)

(52) U.S. Cl.
CPC .............. *A61F 6/02* (2013.01); *A61F 5/0096* (2013.01); *A61F 2250/001* (2013.01)

(58) Field of Classification Search
CPC .... A61F 5/0096; A61F 6/02; A61F 2250/001; A61F 5/37; A61D 19/00; A41B 9/12; A01K 21/00
See application file for complete search history.

(56) References Cited

U.S. PATENT DOCUMENTS

2008/0127986 A1* 6/2008 Miller .................. A61F 5/0096
128/883

* cited by examiner

*Primary Examiner* — Ophelia A Hawthorne
(74) *Attorney, Agent, or Firm* — William Lovin & Associates LLC; William R. Lovin (57) ABSTRACT

The invention relates to chastity devices, particularly to size-adjustable male chastity devices that may permanently affixed to the scrotum and penis of the user and are substantially non-removable.

13 Claims, 6 Drawing Sheets

SIZE-ADJUSTABLE MALE CHASTITY DEVICE

CROSS-REFERENCE TO RELATED APPLICATIONS

This application takes benefit of U.S. Provisional Application No. 61/708,801 entitled "Size-Adjustable Male Chastity Device" which was filed on Oct. 2, 2012.

FIELD OF THE INVENTION

The invention relates to chastity devices, particularly to size-adjustable male chastity devices that may be permanently affixed to the scrotum and penis of the user and are substantially non-removable.

BACKGROUND OF THE INVENTION

The invention relates to a size-adjustable male chastity device for protracted wear on the male sex organ to prevent sexual intercourse and masturbation.

In the prior art, a chastity belt is a locking item of clothing designed to prevent sexual intercourse and masturbation as well as to protect the wearer from sexual temptation. Chastity belts and related devices have a long human history. According to some, the chastity belt was used as an anti-temptation device during the Crusades. When the knight left for the Holy Lands on a Crusade, often his Lady would wear a chastity belt to preserve her faithfulness to him. Male chastity belts are also known in the prior art. U.S. Pat. No. 995,600 (Surgical Appliance) was developed, for example, to prevent masturbation by the mentally ill.

Modern devices range from simple leather or plastic toys commonly sold by adult stores to expensive high-security stainless steel devices. A chastity cage, also referred to as a "ball trap" device, is a device which encloses the male genitals to prevent stimulation and erection. Most such chastity cages have two parts: a ring seated around the base of the penis behind the scrotum and a capped tube, into which the flaccid penis is inserted. The tube is perforated to allow fluid to drain. Some designs have a curved or angled tube to make erections uncomfortable. The two parts mate together on hinges or pins and are secured, usually with a padlock. When the device is locked, the testicles are trapped in the gap between the penis tube and the ring that is ostensibly narrow enough to prevent the testicles, and therefore the penis, from being pulled out. An exemplary device is disclosed in U.S. Pat. No. 7,578,296 (Male Chastity Apparatus, Method, and System) and its continuing application, U.S. Pat. No. 8,007,431. Such chastity cage must be properly sized, fitted and adjusted in order to be secure and not cause physical damage. Unsurprisingly, ring size and spacing are the two most important adjustments that can be made. A ring that is too tight will cut off blood flow, potentially cause physical damage, and is extremely uncomfortable to wear while one that is too loose will not be secure.

As a result, the ring of such devices is often-times worn too loose, rendering it possible to remove the testicles, and thus penis, from the device thus defeating the main purpose of the device in the process. Moreover, the space, albeit small, between the ring tube is often sufficiently large to allow the user to merely remove only the penis. Aftermarket products are available to prevent this occurrence typically by installing a short, angled plastic "tongue" from the pin holding the ring and the tube together such that the tongue protrudes into the shaft of the device and artificially restricts its diameter. As a result, the shaft of the penis is held between the tongue and the inferior aspect of the tube. While more secure, even this device may be defeated because the beveled tongue only serves to secure the anterior aspect of the corona of the penis, leaving the inferior aspect of the tube unaffected where the smoother, less pronounced frenular area of the glans of the penis can slide by. Because of this asymmetric application of restraining force it is thus possible to extract the penis. Accordingly, as a practical matter the successful utilization of these devices usually devolves to selecting a ring and spacer sufficiently small, and thus uncomfortable, to retain the testicles and penis securely inside.

What is needed then is an improvement over the prior art that allows a user to: 1) Self-select a comfortably sized ring and from a multiplicity of spacers to ensure wearing comfort; 2) Self-select a comfortably sized spacer from a multiplicity of spacers to also ensure wearing comfort; and, 3) Ensure that the penis remains in the tube by applying symmetrical restraining forces to the corona of the penis such that the penis is permanently secured within the tube of the device. By this means of this more comfortably worn, improved device even if the testicles are removed from the ring the penis may not be withdrawn from the tube.

SUMMARY OF THE INVENTION

In a first embodiment of the present invention, the size-adjustable male chastity device comprises a ventilated cage housing comprising a shaft portion with a base configured to encase the shaft of the penis of a user and a head portion to encase the head of the penis. A hinged insert with two hinged arms each with at least one anti-pullout projection, mates with and surrounds the cage housing such that the anti-pullout projections extend into the lumen of the cage housing thus causing a snug, secure fit of the cage housing and hinged arms around the penis of the user when the hinged insert is in its closed and locked position. These anti-pullout projections may be angled or beveled forward towards the glans of the penis so that the glans of the penis may not be removed from the cage housing and device. A hinged ring is configured to firmly encircle the user's penis and scrotum from the superior, proximal aspect of the base of the penis to the posterior aspect of the scrotum. The hinged ring serves as the support base for the remainder of the device. A locking pin spacer couples the hinged ring to the cage housing (and enclosing hinged insert) surrounding the penis. A locking pin passes distally through the hinged ring, the locking pin spacer, the base of the cage insert, and protrudes a short distance beyond the closed distal ends of the arms of the hinged insert. In this configuration, the bale of a lock, such as a padlock, may be passed through the closed distal ends of the arms of the hinged insert and the distal end of the locking pin to lock the device on the user.

The device is used in the following manner: First, the hinged ring is placed around the user's scrotum and penis and locked by passing the locking pin through the mated distal ends of each arm of the hinged ring such that the locking pin extends distally away from the hinged ring. Next, the locking pin spacer is attached to the back of the cage housing. Next, the penis is inserted into the cage housing such that the attached locking pin spacer extends proximally towards the hinged ring. Next, the locking pin spacer and cage housing are attached to the hinged ring by means of passing the locking pin through a longitudinally disposed tubular cavity in the locking pin spacer and a concentric hole in the back-plate of the cage housing. Next, the arms of the hinged insert are opened and mated with the cage housing. Next, the arms of the hinged insert are closed, and the mated distal ends of each arm of the hinged insert form a cavity around the distal end of the locking pin where it protrudes from the distal (front) surface of the back-plate of the cage housing. Simultaneously, the anti-pullout projections of the hinged insert are firmly insinuated in the shaft of the penis. In this configuration, the bale of a small lock such as a padlock may be passed through a second cavity formed by the mated ends of the hinged insert and a cavity in the distal end of the locking pin. By this means the cage housing, locking pin spacer, and hinged ring are permanently drawn together while the hinged insert is permanently closed on the shaft of the penis and locked to the cage housing. In an alternative embodiment, the male chastity device can be used without the hinged insert.

DESCRIPTION OF THE DRAWINGS

The invention will be described with reference to the accompanying drawings, in which like elements are referenced with like numerals:

FIG. 1a is a isometric view of a cage housing for a size-adjustable male chastity device according to one embodiment of the invention showing: 1) The back-plate with locking pin cavity; 2) The shaft portion including the grooves for mating with the hinged insert and the ventilation holes; and, 3) The head portion including the urinary cavity for toilet use;

FIG. 1b is a front view of the cage housing for the size-adjustable male chastity device of FIG. 1a;

FIG. 1c is a right view of the cage housing for the size-adjustable male chastity device of FIG. 1a;

FIG. 1d is a back view of the cage housing for the size-adjustable male chastity device showing the back-plate and the open end of the cage housing of FIG. 1a;

FIG. 2a contains an isometric view and an exploded isometric view of the hinged insert device for mating to the cage housing of the size-adjustable male chastity device according to one embodiment of the invention showing: 1) Two arms rotatable about a hinge to open and to close the hinged insert, each arm equipped with: a) An arced-shape cavity formed in its distal end such that when approximated the two arc-shaped cavities form a unitary longitudinal locking pin cavity configured to accept the locking pin; and, b) A transverse cavity formed in its distal end such that when approximated the two transverse cavities form a unitary lock bale cavity that perpendicularly intersects the locking pin cavity thus allowing the bale of a small padlock or other lock to secure the hinged insert to the end of the locking pin in its closed condition; and, 2) One or more medially directed anti-pullout projections disposed along the medial edge of each arm;

FIG. 2b is a front view of the hinged insert in its closed position for mating to the cage housing of the size-adjustable male chastity device of FIG. 2a;

FIG. 2c is a right side view of a hinged insert in its closed position for mating to the cage housing of a size-adjustable male chastity of FIG. 2a;

FIG. 2d is a back view of the hinged insert in its closed position for mating to the cage housing of the size-adjustable male chastity device of FIG. 2a;

FIG. 3b is a front view of the locking pin spacer for mating the hinged ring to the cage housing that serves to stabilize the cage housing of the size-adjustable male chastity device of FIG. 3a;

FIG. 3c is a right side view of the locking pin spacer for mating the hinged ring to the cage housing that serves to stabilize the cage housing of a size-adjustable male chastity of FIG. 3a;

FIG. 3d is a back view of the locking pin spacer for mating the hinged ring to the cage housing that serves to stabilize the cage housing of the size-adjustable male chastity device of FIG. 3a;

FIG. 4b is a front view of the locking pin for connecting the hinged ring, the locking pin spacer, the hinged insert, and the cage housing into a single unit according to one embodiment of a size-adjustable male chastity device of FIG. 4a;

FIG. 4c is a right side view of the locking pin for connecting the hinged ring, the locking pin spacer, the hinged insert, and the cage housing into a single unit according to one embodiment of a size-adjustable male chastity device of FIG. 4a;

FIG. 4d is a back view of the locking pin for connecting the hinged ring, the locking pin spacer, the hinged insert, and the cage housing into a single unit according to one embodiment of a size-adjustable male chastity device of FIG. 4a;

FIG. 5b is a front view of the hinged ring device in its closed position for mating to the cage housing of the size-adjustable male chastity device of FIG. 5a;

FIG. 5c is a right side view of a hinged ring device in its closed position for mating to the cage housing of a size-adjustable male chastity of FIG. 5a;

FIG. 5d is a back view of the hinged ring device in its closed position for mating to the cage housing of the size-adjustable male chastity device of FIG. 5a;

DETAILED DESCRIPTION OF THE INVENTION

Referring to FIGS. 1a through 7b, in a first embodiment of a size-adjustable male chastity device 10 comprises: 1) Ventilated cage housing 20 with laterally disposed anti-pullout grooves 27; 2) Hinged insert 30 that mates with and surrounds cage housing 20 so that anti-pullout projections 34 penetrate through laterally disposed anti-pullout grooves 27 in cage housing 20 such that cage housing 20 remains permanently affixed around the penis of the user when hinged insert 30 is in its closed and locked position; 3) A plurality of hinged rings 40 of various diameters configured to be placed between the superior, proximal aspect of the user's penis and the posterior aspect of the user's scrotum; 4) A plurality of locking pin spacers 50 of various lengths that mate with hinged ring 40 and cage housing 20 to stabilize and connect hinged ring 40 and cage housing 20 while simultaneously adjusting the distance between them to maximize wearing comfort; and, 5) a plurality of locking pins 60 of various lengths that penetrate through collinear locking pin cavities in hinged ring 40, locking pin spacer 50, cage housing 20, and hinged insert 30 and having transverse lock bale cavity 61 to accept bale 71 of a lock such as padlock 70 to secure size-adjustable male chastity device 10 on the penis of the user. A plurality of locking pin spacers 50 and locking pins 60 of differing lengths are available, differing sizes being used to accommodate the device to different penis lengths. In one embodiment, size-adjustable male chastity device 10 can be used without hinged insert 30, by substituting securing cap 39 to allow the device to be locked.

Cage housing 20 is comprised of shaft portion 21 configured to encase the shaft of the penis and head portion 22 to encase the head of the penis. Shaft portion 21 is ventilated as is head portion 22. Head portion 22 provides urinary cavity 23 that approximates the meatus of the urethra, to allow urination when size-adjustable male chastity device 10 is being worn. Back-plate 24 is positioned at the proximal end of shaft portion 21 of cage housing 20 and is located toward the user's body. Back-plate 24 comprises locking pin cavity 25 at the top configured to accept the distal end of locking pin 60. Back-plate 24 further comprises at least two mating cavities 26 to accept distally projecting mating clips 51 projecting from the distal surface of locking pin spacer 50. At least a pair of anti-pullout grooves 27 configured to accept hinged insert 30 when closed are provided on substantially opposite sides of the shaft portion 21 of cage housing 20.

Those having skill in the art will recognize that while the first embodiment of the present invention comprehends that each of anti-pullout grooves 27 will be a unitary groove, such need not be the case. Rather, each of anti-pullout grooves 27 may be comprised of a multiplicity of smaller, contiguous grooves, or cavities formed in cage housing 20.

Hinged insert 30 comprises two arms 31 and 32 that are rotatable about hinge pin 35 to open and to close, where arms 31 and 32 are of a size to mate with anti-pullout grooves 27 formed in cage housing 20 to closely hug the penis of the user when in cage housing 20. Each of arms 31 and 32 comprise one or more rib supports 33 with one or more medially directed, anti-pullout projections 34 disposed along the inner aspects of each of arms 31 and 32 such that when hinged insert 30 is placed around cage housing 20 and closed while on the penis of the user, anti-pullout projections 34 are directed medially through anti-pullout grooves 27, into the lumen of cage housing 20, and thus into the shaft of the penis. In another embodiment, anti-pullout projections 34 may be angled slightly forward towards the glans of the penis. In another embodiment, anti-pullout projections 34 may be beveled along their innermost edges such that each is slightly longer along its most distal surface and slightly shorter on its most proximal surface. Further, anti-pullout projections 34 may be of varying lengths. In all these embodiments, cage housing 20 and hinged insert 30 may not be removed from the penis when hinged insert 30 is closed around cage housing 20 the penis. Hinged insert 30 can function this way because the glans of the penis ordinarily is of greater diameter and firmer than the shaft and when anti-pullout projections 34 are extended through both sides of cage housing 20 and compress into the shaft they necessarily provided insufficient clearance for removal of the glans.

The distal ends of each arm 31 and 32 of hinged insert 30 comprise mating lips 36 and longitudinally disposed arced cutouts 37a, such that when arms 31 and 32 of hinged insert 30 are in their closed position, the two longitudinally disposed arced cutouts 37a mate to form locking pin cavity 37b configured to accept the distal end of locking pin 60. Hinged insert 30 may further be configured to fit over retaining projection 29 that may be disposed extending downward from the inferior, outer surface of shaft portion 21 of cage housing 20 such that, when hinged insert 30 is closed about cage housing 20, it is substantially prevented from moving or sliding with respect to cage housing 20. Mirror image transverse cavities 38a perpendicularly formed through mating lips 36 at the distal ends of each of arms 31 and 32 of hinged insert 30 are provided so that when arms 31 and 32 of hinged insert 30 are closed they form transverse lock bale cavity 38b such that it perpendicularly intersects locking pin cavity 37b thus allowing bale 71 of padlock 70 to be passed through transverse lock bale cavity 38b (and transverse lock bale cavity 61 in the distal end of locking pin 60 when the device is assembled and worn) to secure hinged insert 30 in the closed position.

Figures 7A, 7B:
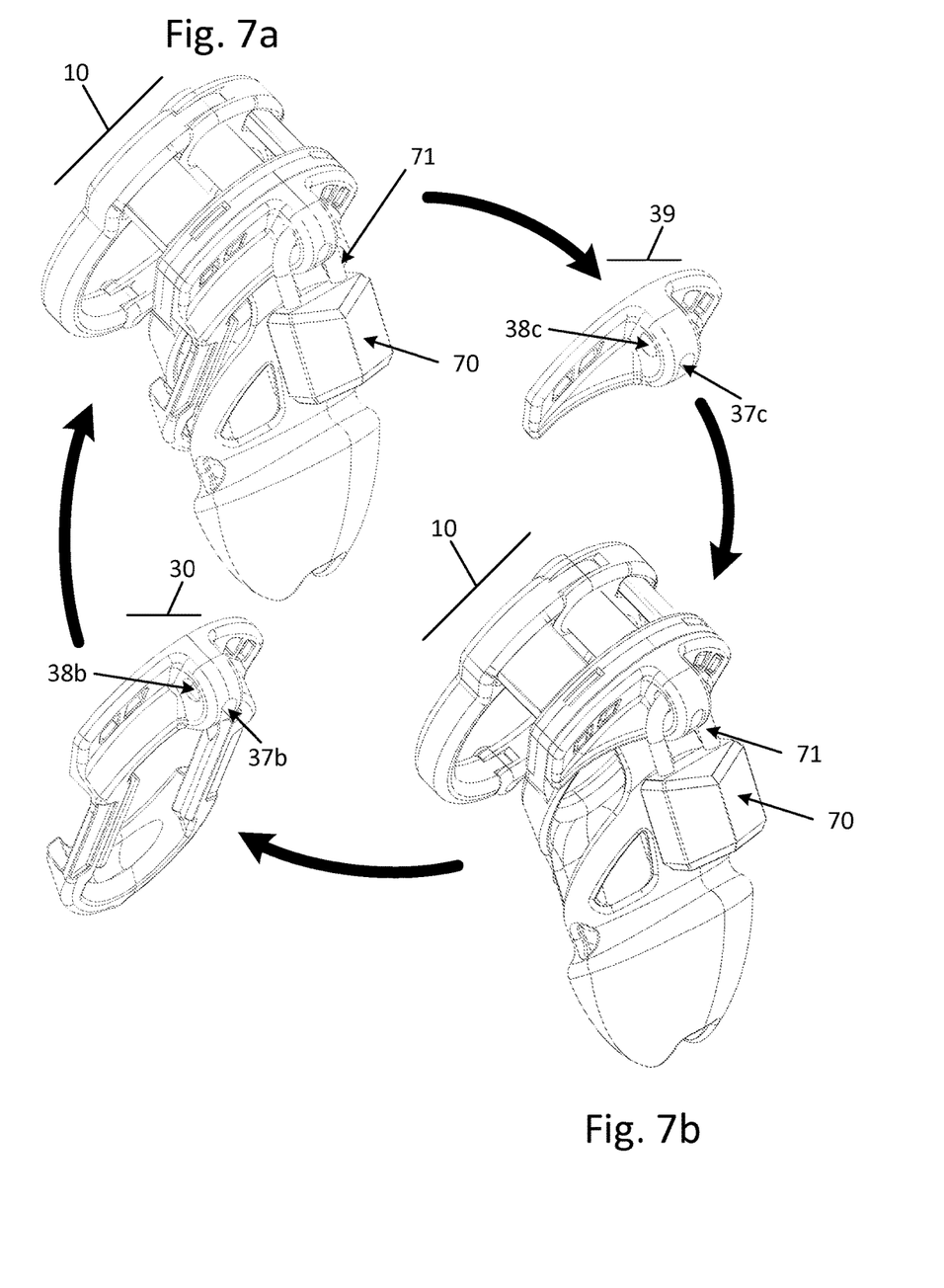
FIG. 7a is an isometric view of a size-adjustable male chastity device according to one embodiment of the invention as assembled and locked as in use.
FIG. 7b is an isometric view of a size-adjustable male chastity device according to an alternative embodiment of the invention as assembled and locked as in use.

If the user wishes to wear the device without hinged insert 30, securing cap 39 may be substituted to cover the end of locking pin 60 as it extends through cage housing 20. Like hinged insert 30, securing cap 39 is equipped with perpendicularly intersecting transverse lock bale cavity 38c and locking pin cavity 37c thus allowing bale 71 of padlock 70 to be passed through transverse lock bale cavity 38c (and transverse lock bale cavity 61 in the distal end of locking pin 60 when the device is assembled and worn). Indeed, as shown in FIGS. 7a and 7b, it is possible to freely interchange between size-adjustable male chastity device 10 with hinged insert 30 and size-adjustable male chastity device 10 with securing cap 39 as desired.

As discussed above, those having skill in the art will recognize that while the first embodiment of the present invention comprehends that each of anti-pullout grooves 27 will be a unitary groove, each of anti-pullout grooves 27 may be comprised of a multiplicity of smaller, contiguous grooves, or cavities formed in cage housing 20. Correspondingly, while the first embodiment of the present invention comprehends that each of anti-pullout projections 34 will be a unitary projection, such need not be the case. Rather, each of anti-pullout projections 34 may be comprised of a multiplicity of smaller, contiguous projections formed in arms 31 and 32 of hinged insert 30.

Hinged ring 40 comprises two arms 41 and 42 that are rotatable about hinge pin 43 to open and to close. Each of arms 41 and 42 further comprising longitudinally disposed cavities 44a at distal ends arms 41 and 42 when hinged ring 40 is in the open position, such that longitudinally disposed cavities 44a overlap when hinged ring 40 is in its closed position thus forming locking pin cavity 44b. Locking pin cavity 44b is sized to accept locking pin 60. Further, an indentation 46 may be included in the proximal surface of arm 41 of hinged ring 40 to allow for a flush fit of the head of locking pin 60 when it is inserted through locking pin cavity 44b. Each of arms 41 and 42 of hinged ring 40 further comprise a one or more grooved sleeve portions 45 that extend above each end of arms 41 and 42 of hinged ring 40. Grooved sleeve portions 45 are sized to accept arc-shaped ends 52 of locking pin spacer 50.

Locking pin spacer 50 is substantially arc-shaped and comprises two proximally projecting arc-shaped ends 52 that conform to the shape of grooved sleeve portions 45 in hinged ring 40 such that arc-shaped ends 52 may be inserted to reside within grooved sleeve portions 45. Locking pin spacer 50 also comprises proximally projecting locking pin tube 53 with its collinear locking pin cavity 54. Locking pin spacer 50 further comprises distally projecting mating clips 51 that interlock with mating cavities 26 on the proximal surface of back-plate 24 of cage housing 20 to connect hinged ring 40 to cage housing 20.

Locking pin 60 has head 62 and a shaft and is sized to be securely inserted through locking pin cavity 44b of hinged ring 40 such that head 62 resides in indentation 46 in the proximal surface of arm 41 to allow for a flush fit of head 62 of locking pin 60. It will be apparent to those having skill in the art that either, or both, of head 62 and/or the actual shaft of locking pin 60 may have an oval, square, or any other non-circular cross-section to prevent locking pin 60 from rotating when inserted. If head 62 of locking pin 60 is non-circular, indentation 46 in the proximal surface of arm 41 of hinged ring 40 must be suitably altered to match. Locking pin 60 further comprises transverse lock bale cavity 61 formed through its distal end. When used, locking pin 60 passes in turn through: 1) Locking pin cavity 44b of hinged ring 40; 2) Locking pin cavity 54 collinearly disposed though locking pin tube 53 of locking pin spacer 50; 3) Locking pin cavity 25 in back-plate 24 of cage housing 20; and, 4) Locking pin cavity 37b formed when arms 31 and 32 of hinged insert 30 are in their closed position in anti-pullout grooves 27 of cage housing 20. When properly inserted, transverse lock bale cavity 61 in the distal end of locking pin 60 communicates with transverse lock bale cavity 38b also formed when arms 31 and 32 of hinged insert 30 are in their closed position in anti-pullout grooves 27 of cage housing 20. By this means bale 71 of padlock 70 may be passed simultaneously through transverse lock bale cavity 38b and transverse lock bale cavity 61, thus securing size-adjustable male chastity device 10 on the penis of the user.

Figures 6A, 6B:
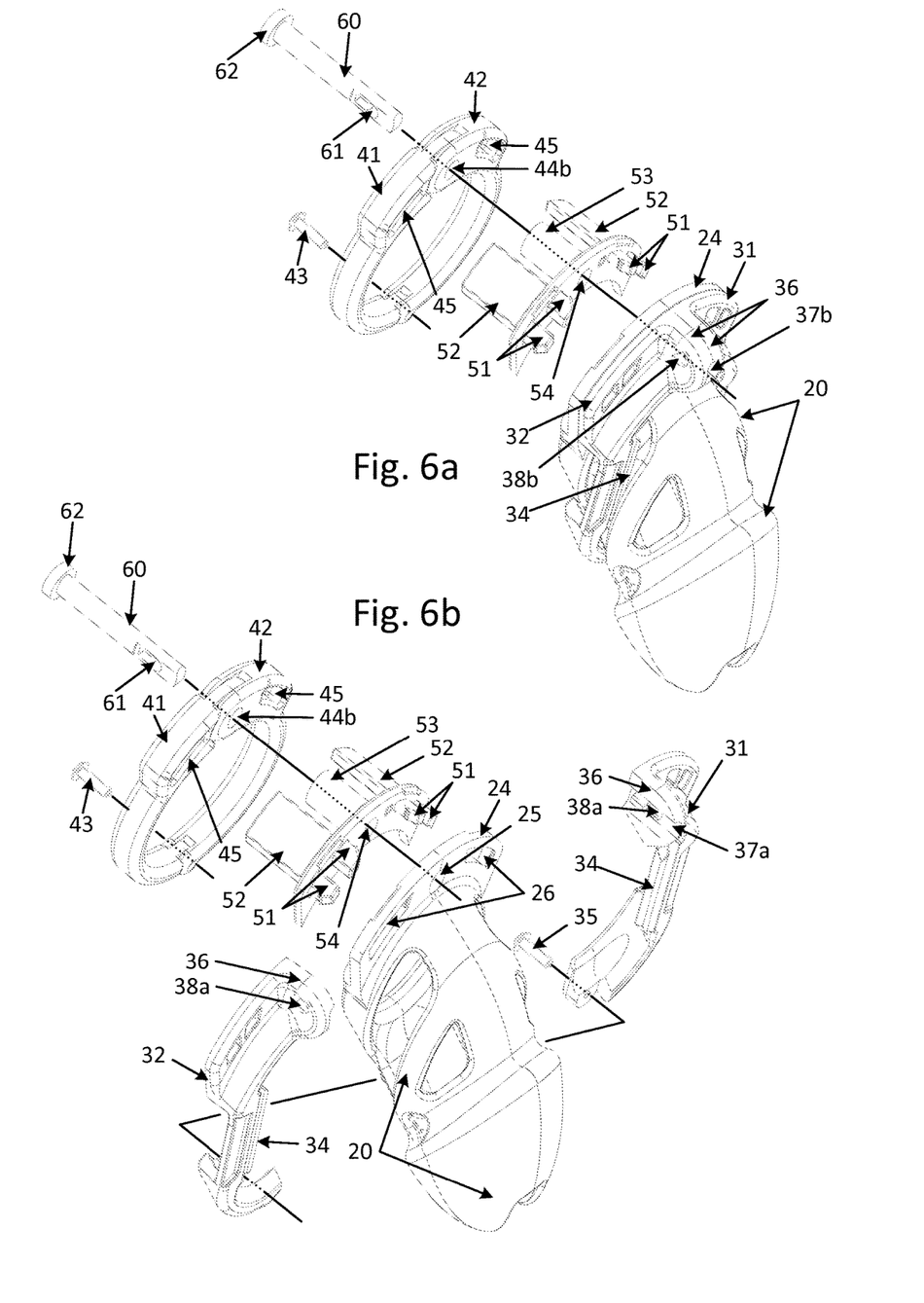
FIGS. 6a and 6b are exploded isometric views of the locking pin, hinged ring device, locking pin spacer, the cage housing, and the hinged insert detailing how these components are assembled together to use a size-adjustable male chastity device according to one embodiment of the invention.

A method of using the first embodiment of size-adjustable male chastity device 10 comprises the following steps: 1) Selecting hinged ring 40 according to the size, comfort or other desires of the user; 2) Placing arms 41 and 42 of hinged ring 40 in their open position around the superior, proximal aspect of the base of the penis to the posterior aspect of the scrotum; 3) Closing arms 41 and 42 of hinged ring 40 such that longitudinally disposed cavities 44a at distal ends arms 41 and 42 overlap forming locking pin cavity 44b such that locking pin cavity 44b lies along the superior aspect of the penis; 4) Placing locking pin 60 through locking pin cavity 44b in hinged ring 40 where transverse lock bale cavity 61 of locking pin 60 is distally disposed from the body of the user and head 62 of locking pin 60 is flush in indention 46; 5) Placing cage housing 20 over the penis of the user; 6) Selecting locking pin spacer 50 according to the size, comfort, or other desires of the user; 7) Inserting distally projecting mating clips 51 of locking pin spacer 50 through mating cavities 26 in the proximal surface of back-plate 24 of cage housing 20 to connect locking pin spacer 50 to cage housing 20; 8) Inserting arc-shaped ends 52 of locking pin spacer 50 into grooved sleeve portions 45 in hinged ring 40 such that arc-shaped ends 52 reside within grooved sleeve portions 45 while simultaneously passing locking pin 60 protruding from the distal surface of hinged ring 40 successively through: a) Locking pin cavity 54 of locking pin spacer 50; and, b) Locking pin cavity 25 of back-plate 24 of cage housing 20; 9) Placing arms 31 and 32 of hinged insert 30 around cage housing 20 such that arms 31 and 32 are disposed in anti-pullout grooves 27 of cage housing 20; 10) Closing arms 31 and 32 of hinged insert 30 such that anti-pullout projections 34 are directed medially through anti-pullout grooves 27 of cage housing 20 and into the shaft of the penis such that hinged insert 30 and enclosed cage housing 20 may not be removed from the penis; 11) Inserting locking pin 60 through locking pin cavity 37b formed when arms 31 and 32 of hinged insert 30 are in their closed position; and, 11) Inserting bale 71 of padlock 70 simultaneously through: a) Transverse lock bale cavity 38b formed when arms 31 and 32 of hinged insert 30 are in their closed position; and, b) Transverse lock bale cavity 61 at the distal end of locking pin 60 thus securing size-adjustable male chastity device 10 on the penis of the user. Some of these steps may be performed substantially simultaneously. However, the assembly of size-adjustable male chastity device 10 preferably entails that locking pin spacer 50 be attached to cage housing 20 before cage housing 20 with attached locking pin spacer 50 is connected to hinged ring 40. Once these pieces are assembled, the user may attach hinged insert 30 or securing cap 39.

Cage housing 20, locking pin spacer 50, and hinged ring 40 are preferably made of polycarbonate, which is also known by the names Lexan®, Makrolon® and Makroclear®, among others. Polycarbonates are thermoplastic polymers that are easily worked, molded, and thermoformed. Hinged insert 30, securing cap 39, and locking pin 60 may also be made of polycarbonate, but are preferably made of acetal, a polyacetal of formaldehyde. Those having skill in the art will readily recognize that any of all of these components may be made of numerous alternative materials, such as nylon, carbon reinforced composite, and various metals like aluminum and steel.

Figures 1A, 1B:
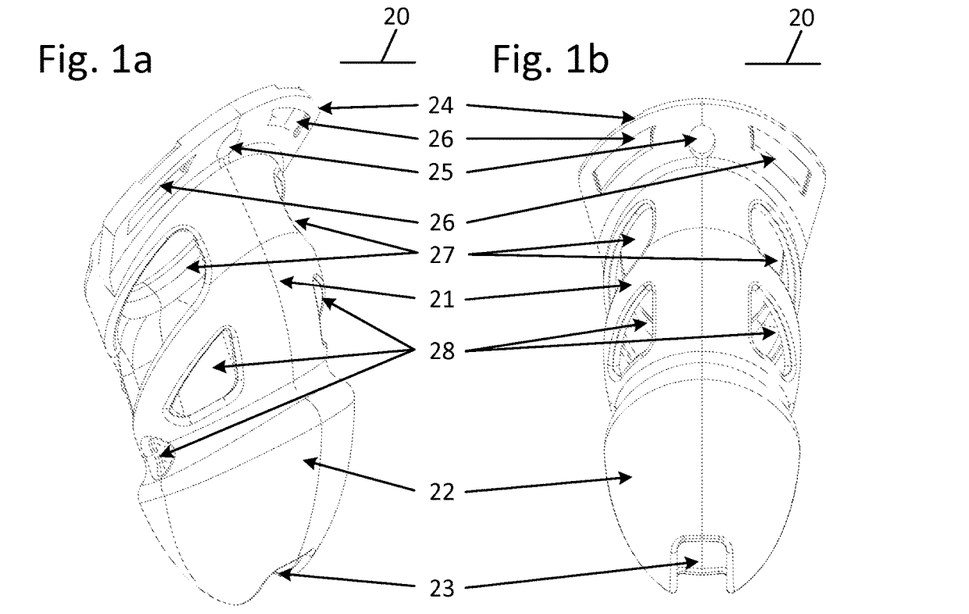
Figures 1C, 1D:
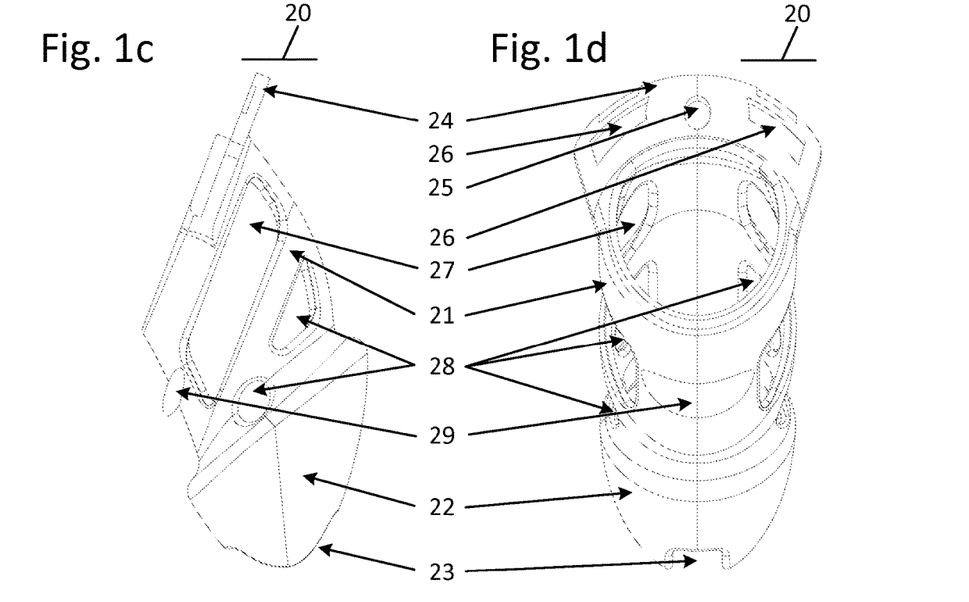
Figures 2A, 2B:
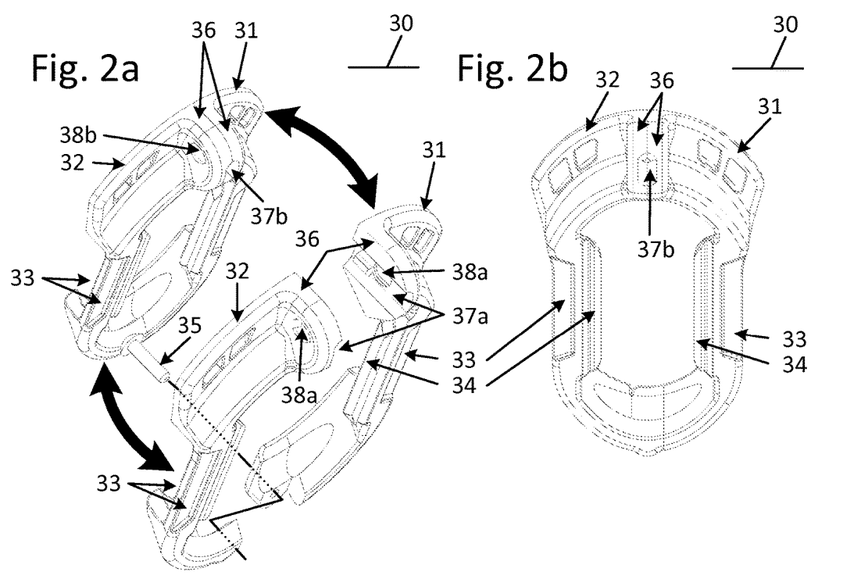
Figure 2C:
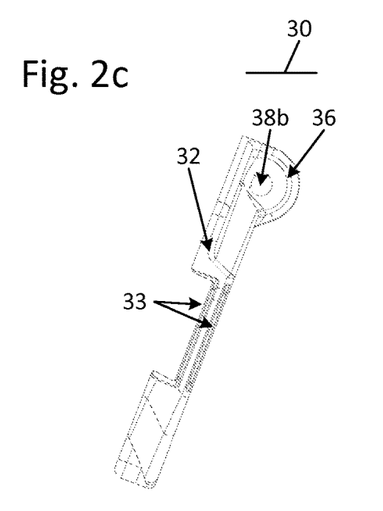
Figure 2D:
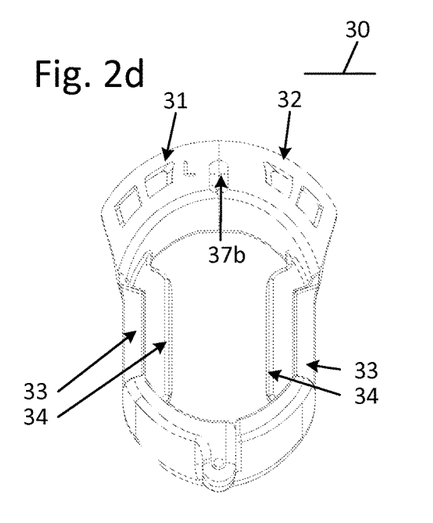

In this embodiment, the length from back-plate 24 of cage housing 20 to the tip of cage housing 20 is between about 57 mm to 64 mm. The height of cage housing 20 as measured from the lowest point to the highest point (i.e. the top of back-plate 24), is about 86 mm. The width, as measured as the widest point between opposite sides of shaft portion 21 of cage housing 20, is about 46 mm. The thickness of the material comprising cage housing 20, is about 2.5 mm. When assembled, size-adjustable male chastity device 10 has an angle of declination between about 44-50° down from vertical. The inner diameter of the cavity in back-plate 24 for insertion of the penis is about 35 mm. Back-plate 24 is preferably in the form of an oval, an elliptical, or an egg shape, with a thickness of about 6 mm. Shaft portion 21 of cage housing 20 that houses the penis can ranges from about 28-30 mm in diameter to about 23-25 mm in diameter. The distance between the tangential longitudinal centerlines of anti-pullout grooves 27 formed in the sides of cage housing 20 is about 23 mm. Anti-pullout grooves 27 may have a taper angle of about 20-30° as measured between back-plate 24 and the outer surface of cage housing 20. Ventilation holes 28 in cage housing 20 may vary in size as can urinary cavity 23 in head portion 22 of cage housing 20 to allow toilet use. In this first embodiment urinary cavity 23 preferably ranges from about 38-50 mm in length and about 8-10 mm in width.

Figure 5A:
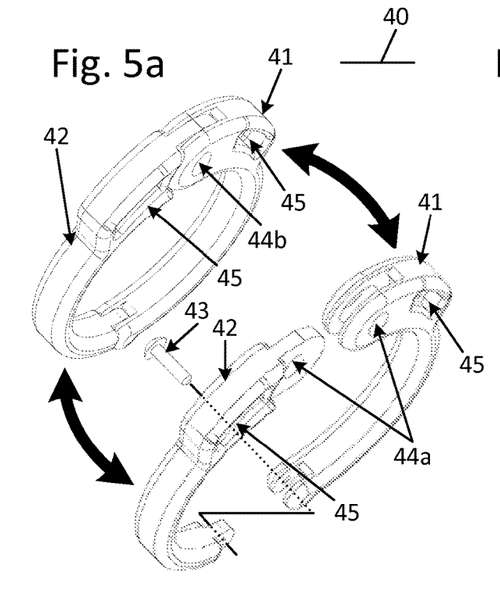
FIG. 5a contains an isometric view and an exploded isometric view of the hinged ring device configured to be placed between the user's body and the user's scrotum in its closed position serving to support the locking pin spacer of the size-adjustable male chastity device according to one embodiment of the invention showing: 1) Two arms rotatable about a hinge to open and to close the hinged ring, each arm with a cavity at its distal end such that when the two cavities approximated they form a unitary locking pin cavity configured to accept the locking pin; and, 2) Cavities to accept the proximally projecting protrusions of the locking pin spacer.
Figure 5B:
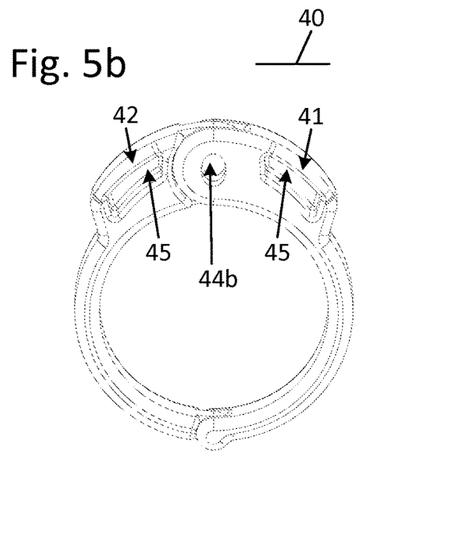
Figure 5C:
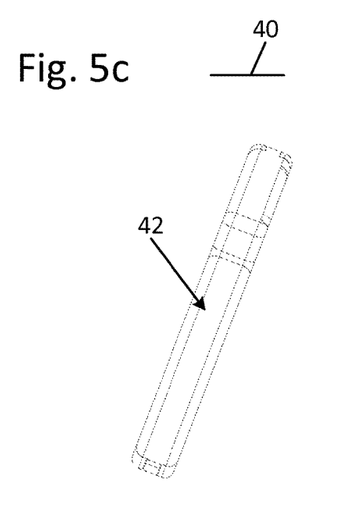
Figure 5D:
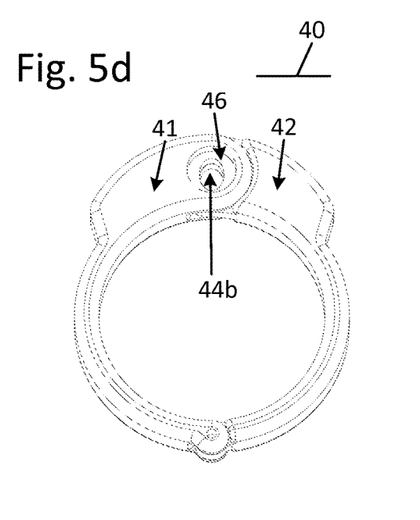

As mentioned previously, hinged ring 40 may be provided in a variety of arbitrary sizes such as small, medium, large, and extra-large to accommodate variations in personal anatomy and user preference as illustrated in the following table:

|  | Small | Medium | Large | Extra-Large |
| --- | --- | --- | --- | --- |
| Outer Diameter | 54 mm | 58 mm | 61.5 mm | 64 mm |
| Inner Diameter | 40 mm | 44 mm | 46.5 mm | 48.5 mm |
| Thickness | 5 mm | 5 mm | 5.5 mm | 5.5 mm |
| Width | 9 mm | 9 mm | 9 mm | 9 mm |

Generally, the inner diameter of hinged ring 40 may vary from about 30 mm to about 60 mm. However, as the table above demonstrates, the inner diameter of hinged ring 40 according to embodiments of the invention disclosed herein preferably ranges from about 40 mm to about 48.5 mm.

Figure 3A:
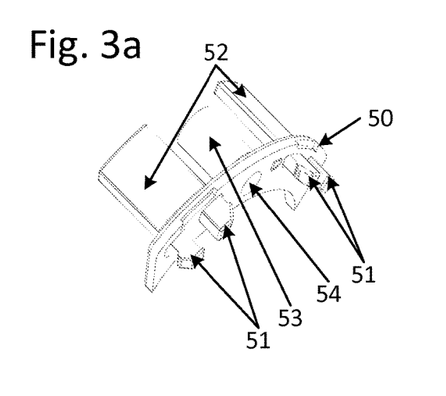
FIG. 3a is an isometric view of the locking pin spacer for mating the hinged ring to the cage housing that serves to connect the hinged ring to the cage housing of the size-adjustable male chastity device according to one embodiment of the invention showing: 1) Distally projecting mating clips that affix the locking pin spacer to mating cavities in the proximal surface of the cage housing; 2) Proximally projecting protrusions with arc-shaped ends for mating with associated cavities in the hinged ring; and, 3) The proximally projecting locking pin tube with its collinear locking pin cavity.
Figure 3B:
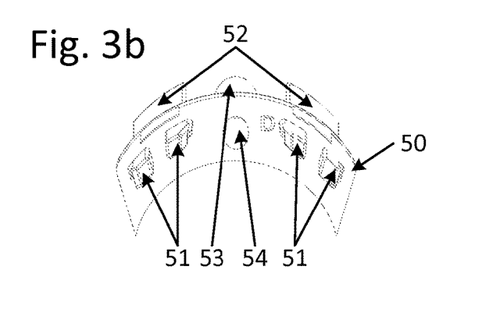
Figure 3C:
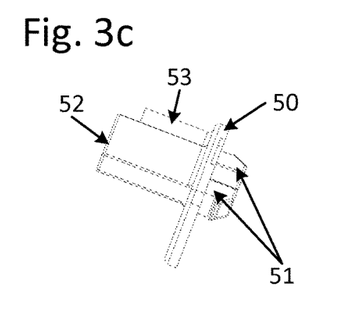
Figure 3D:
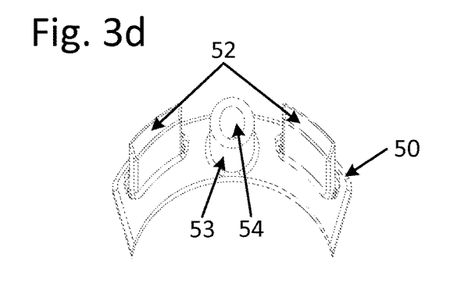
Figure 4A:
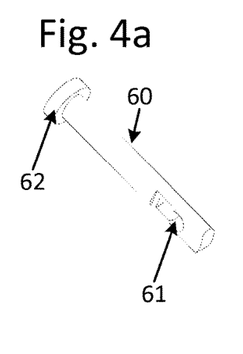
FIG. 4a is an isometric view of the locking pin for connecting the hinged ring, the locking pin spacer, the hinged insert, and the cage housing into a single unit according to one embodiment of the invention showing the slotted cavity for accepting a small padlock or other lock to secure the hinged ring, the locking pin spacer, the hinged insert, and the cage housing into a single unit.
Figure 4B:
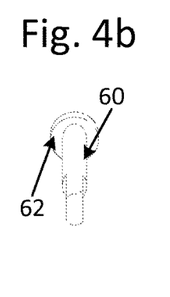
Figure 4C:
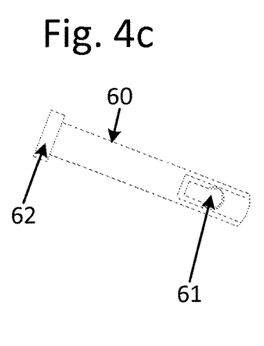
Figure 4D:
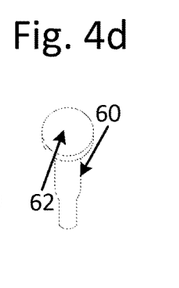

Similarly, locking pin spacer 50 and locking pin 60 may also be provided in a variety of arbitrary sizes such as small, medium, large, and extra-large to accommodate variations in personal anatomy and user preference as illustrated in the following table:

|  | Small | Medium | Large | Extra-Large |
| --- | --- | --- | --- | --- |
| Locking Pin Spacer 50 Length | 22 mm | 25 mm | 28.5 mm | 31.5 mm |
| Locking Pin 60 Length | 34 mm | 37 mm | 40 mm | 43 mm |
| Ring-Cage Distance | 6.5 mm | 10 mm | 13 mm | 15 mm |

In the table above, the dimension associated with locking pin spacer 50 represents its length measured from the proximal aspect of arc shaped ends 52 of locking pin spacer 50 to the distal aspect of distally projecting mating clips 51. The "Ring-Cage Distance" referenced in the above table represents the distance from the distal (front) surface of hinged ring 40 to the proximal (back) surface of back-plate 24 of cage housing 20. Generally, the Ring-Cage Distance may vary from about 3 mm to about 18.5 mm. However, as the table above demonstrates, the Ring-Cage Distance preferably ranges from about 6.5 mm to about 15 mm.

While the present invention has been described in the context of a first and several alternative embodiments, one having skill in the art will recognize that numerous variations and alterations may be conceived of none which detract from the essential elements of the invention, to wit: 1) Hinged ring 40 is placed around the penis and scrotum from the superior, proximal aspect of the base of the penis to the posterior aspect of the scrotum and locked in place by locking pin 60 proceeding distally away from hinged ring 40; 2) Locking pin 60 is passed through locking pin spacer 50 and attached cage housing 20 with the user's penis inside; 3) Cage housing 20 is enclosed within and by arms 31 and 32 of hinged insert 30 such that anti-pullout projections 34 of arms 31 and 32 compress into the shaft of the penis and the closed distal mating lips 36 of arms 31 and 32 form: a) Locking pin cavity 37b surrounding the distal end of locking pin 60; and, b) Transverse lock bale cavity 38b perpendicularly intersecting locking pin cavity 37b; and, 4) Hinged ring 40, locking pin spacer 50, cage housing 20, and hinged insert 30 are all secured together by means of bale 71 of padlock 70 passed simultaneously through transverse lock bale cavity 38b and transverse lock bale cavity 61 in the distal end of locking pin 60 such that the assembled size-adjustable male chastity device 10 may not be removed by the user until unlocked.

While the invention has been described in connection with what are considered to be the most practical and preferred embodiments, it is to be understood that the invention is not to be limited to the disclosed embodiments, but on the contrary is intended to cover various modifications and equivalent arrangements included within the spirit and scope of the disclosure. Particularly, those having skill in the art will recognize that while the invention comprehends that each of anti-pullout grooves 27 will closely adjoin back-plate 24 of cage housing 20 such that when in use hinged insert 30 may be locked to the rest of the components comprising size-adjustable male chastity device 10, such need not be the case. For example, a second set of grooves disposed further along shaft portion 21 of cage housing 20 may be supplied and a second hinged insert 30 requiring a separate padlock 70 may be used. Still another alternative hinged insert 30 requiring a separate padlock 70 may be supplied that affixes to cage housing 20 such that anti-pullout projections 34 penetrate though ventilation holes 28, and so on.

What is claimed is:

1. A size adjustable male chastity device, comprising:
   a. a hinged ring comprising two first pivoting arms to be placed around a user's body from a superior, proximal aspect of a base of a penis to a posterior aspect of a scrotum, such that when said hinged ring is closed distal ends of said first pivoting arms overlap forming a proximal locking pin cavity;
   b. a cage housing configured to partially contain the penis of the user, said cage housing comprising, at least two anti-pullout grooves, a distal locking pin cavity, and a urinary cavity;
   c. a locking pin spacer further comprising a longitudinally disposed medial locking pin cavity wherein said locking pin spacer is rigidly affixable between said cage housing and said hinged ring such that said proximal, medial, and distal locking pin cavities are collinearly aligned;
   d. a hinged insert comprising two second pivoting arms each with at least one anti-pullout projection such when said second pivoting arms are placed around said cage housing and said hinged insert is closed:
      i. said anti-pullout projections pass through said anti-pullout grooves and into a lumen of said cage housing;
      ii. the distal ends of said second pivoting arms overlap forming a terminal locking pin cavity colliineally aligned with said proximal, medial, and distal locking pin cavities and a first transverse lock bale cavity; and
   e. a locking pin with a second transverse lock bale cavity formed through said distal end, wherein said locking pin is inserted successively through said proximal, medial, distil, and terminal locking pin cavities such that said first and second transverse lock bale cavities are collinearly aligned such that a lock with a bale may be passed through them.

2. A size-adjustable male chastity device of claim 1, wherein a securing cap is substituted for said hinged insert.

3. A size-adjustable male chastity device of claim 1, wherein said anti-pullout projections are angled forward towards the glans of the penis when inserted in said cage housing.

4. A size-adjustable male chastity device of claim 1, wherein said anti-pullout projections are beveled along said innermost edges such that each is longer along said most distal surface and shorter on said most proximal surface.

5. A size-adjustable male chastity device of claim 1, wherein said hinged ring varies in internal diameter from about 40 mm to about 48.5 mm.

6. A size-adjustable male chastity device of claim 1, wherein said locking pin spacer varies in length between about 22 mm and about 31.5 mm.

7. A size-adjustable male chastity device of claim 1, wherein the distance from the distal surface of said hinged ring and a proximal surface of a back-plate of said cage housing varies in length between about 6.5 mm and about 15 mm.

8. A size-adjustable male chastity device of claim 1, wherein said locking pin comprises a head and a shaft at least one of which is oval-shaped in cross-section.

9. A size-adjustable male chastity device of claim 1, wherein said cage housing is an approximately penis-shaped casing comprising a shaft portion and a head portion and further comprising at least one anti-pullout groove along a lateral aspect of each side of the shaft portion and a urinary cavity at said distal end.

10. A size-adjustable male chastity system comprising:
  a. a hinged ring with two arms, each with a first distal end such that when placed around a user's body from a superior, proximal aspect of a base of a penis to a posterior aspect of a scrotum said first distal ends form a proximal locking pin cavity;
  b. a cage housing to partially contain the penis of the user, said cage housing comprising at least two anti-pullout grooves, a urinary cavity, and a distal locking pin cavity;
  c. a locking pin spacer with a longitudinally disposed medial locking pin cavity wherein said locking pin spacer rigidly affixes said cage housing and said hinged ring such that said proximal, medial, and distal locking pin cavities are collinearly aligned;
  d. a hinged insert with two arms, each with a second distal end and a least one medially projecting anti-pullout protrusion such that when placed around said cage housing said anti-pullout protrusions pass through said anti-pullout grooves into a lumen of said cage housing and said second distal ends form a terminal locking pin cavity collinearly aligned with said proximal, medial, and distal locking pin cavities and a first transverse lock bale cavity perpendicularly disposed to said terminal locking pin cavity;
  e. a locking pin with a second transverse lock bale cavity formed through said distal end, wherein said locking pin is inserted successively through said proximal, medial, distal, and terminal locking pin cavities such that said first and second transverse lock bale cavities are collinearly aligned;
  f. a lock with a bale that is passed through said first and second transverse lock bale cavities to lock the size-adjustable male chastity device to the penis and scrotum of a user.

11. A size-adjustable male chastity system of claim 10, wherein a securing cap is substituted for said hinged insert.

12. A size-adjustable male chastity system of claim 10, wherein said locking pin comprises a head and a shaft at least one of which is oval-shaped in cross-section.

13. A method of using a size-adjustable male chastity system of claim 10 comprising the steps of:
  a. selecting a hinged ring according to the size, comfort or other desires of the user;
  b. placing the first arms of said hinged ring in their open position around the superior, proximal aspect of the base of the penis to the posterior aspect of the scrotum;
  c. closing said first arms of said hinged ring such that the distal ends of each of said first arms overlap forming a proximal locking pin cavity aligned along the superior aspect of the penis;
  d. placing a locking pin through said proximal locking pin cavity such that the second transverse lock bale cavity of said locking pin is disposed away from the body of the user;
  e. placing a cage housing with a back-plate affixed to the proximal aspect of said shaft portion, said back-plate further comprising a distal locking pin channel, over the penis of the user;
  f. selecting a locking pin spacer with a longitudinally oriented medial locking pin channel according to the size, comfort, or other desires of the user;
  g. connecting said locking pin spacer to said cage housing; h. connecting said locking pin spacer to said hinged ring while simultaneously passing said locking pin successively through said medial locking pin cavity and said distal locking pin cavity;
  i. placing the second arms of a hinged insert around said cage housing such that said second arms are disposed in the anti-pullout grooves of said cage housing;
  j. closing said second arms of said hinged insert around the distal end of said locking pin such that:
    i. the distal ends of each of said second arms overlap forming a terminal locking pin cavity collinearly aligned with and surrounding the distal end of said locking pin and a first transverse lock bale cavity transversely disposed with respect to said terminal locking pin cavity, said first transverse lock bale cavity further being collinearly aligned with said second transverse lock bale cavity in the distal end of said locking pin; and
    ii. the anti-pullout projections associated with said second arms are directed medially through said anti-pullout grooves of said cage housing and into the shaft of the penis;
  k. inserting the bale of a padlock simultaneously through said first transverse lock bale cavity formed when said distal ends of each of said second arms overlap and said second transverse lock bale cavity formed in the distal end of locking pin thus securing size-adjustable male chastity system on the penis of the user.

* * * * *